(12) United States Patent
Ischdonat (10) Patent No.: US 6,743,337 B1
(45) Date of Patent: Jun. 1, 2004

(54) PROCESS AND APPARATUS FOR DETERMINING THE PROPERTIES OF A TRAVELING MATERIAL WEB

(75) Inventor: Thomas Ischdonat, Bachhagel (DE)

(73) Assignee: Voith Sulzer Papiertechnik Patent GmbH, Heidenheim (DE)

( * ) Notice: Subject to any disclaimer, the term of this patent is extended or adjusted under 35 U.S.C. 154(b) by 0 days.

(21) Appl. No.: 09/531,561

(22) Filed: Mar. 20, 2000

(30) Foreign Application Priority Data

Mar. 19, 1999 (DE) .......................................... 199 12 500

(51) Int. Cl.[7] ............................. D21F 7/06; G01N 21/86
(52) U.S. Cl. ................. 162/198; 162/263; 162/DIG. 6; 250/339.02; 250/339.11; 250/559.04; 250/559.05; 250/559.11; 356/429
(58) Field of Search ................................. 162/198, 199, 162/252, 253, 263, 262, DIG. 6, DIG. 10, DIG. 11; 210/709; 250/339.1, 559.01, 339.02, 339.06, 339.11, 341.7, 341.8, 559.04, 559.05, 559.11, 559.03, 559.07; 700/127, 128, 129; 73/159; 356/429–431

(56) References Cited

U.S. PATENT DOCUMENTS

| 3,614,450 | A | * | 10/1971 | Hill .............................. 250/210 |
| 3,792,271 | A | * | 2/1974 | Sandblom ..................... 250/347 |
| 4,098,641 | A | | 7/1978 | Casey et al. |
| 4,329,591 | A | | 5/1982 | Fujiwara et al. |
| 4,840,706 | A | * | 6/1989 | Campbell .................... 162/198 |
| 4,857,747 | A | * | 8/1989 | Bolton et al. ........... 250/559.24 |
| 4,897,159 | A | * | 1/1990 | Bone et al. ................... 162/260 |
| 4,931,657 | A | * | 6/1990 | Houston et al. ............. 250/225 |
| 5,118,940 | A | * | 6/1992 | Davis et al. ................. 250/308 |
| 5,327,770 | A | * | 7/1994 | Hindle ............................. 73/1 |
| 5,548,120 | A | * | 8/1996 | Parker et al. ................ 250/228 |
| 5,696,591 | A | * | 12/1997 | Bilhorn et al. ............... 356/429 |
| 5,745,365 | A | * | 4/1998 | Parker ..................... 364/469.01 |
| 5,822,070 | A | * | 10/1998 | Syre ........................... 356/419 |
| 6,053,040 | A | * | 4/2000 | Callender et al. .............. 73/159 |
| 6,060,677 | A | * | 5/2000 | Ulrichsen et al. ............ 209/577 |
| 6,229,612 | B1 | * | 5/2001 | Koo ............................ 356/433 |
| 6,259,109 | B1 | * | 7/2001 | Dalmia et al. ........... 250/559.08 |
| 6,548,812 | B1 | * | 4/2003 | Schumacher ........... 250/339.02 |

FOREIGN PATENT DOCUMENTS

| DE | 297711 | 10/1983 | .......... G01N/21/62 |
| DE | 3634869 | 4/1988 | .......... G02B/27/00 |
| DE | 4131835 | 3/1993 | .......... G01N/21/89 |
| DE | 19624905 | 1/1998 | .......... G01N/21/86 |
| DE | 29623620 | 2/1999 | .......... G01N/21/86 |
| EP | 137696 | 4/1985 | .......... G01N/21/35 |
| EP | 0 390 623 | * 10/1990 | .......... G01N/21/59 |
| WO | 93/15389 | 8/1993 | .......... G01N/15/02 |
| WO | 95/08019 | 3/1995 | ............ D21C/5/02 |
| WO | 95/31709 | 11/1995 | .......... G01N/21/31 |
| WO | 98/36264 | 8/1998 | .......... G01N/21/35 |
| WO | 98/40727 | 9/1998 | |

OTHER PUBLICATIONS

E. Herrala et al., "Imaging Spectrograph and Camera Solutions For Industrial Applications" International Journal of Pattern Recognition and Artificial Intelligence, vol. 10, No. 1 (1996) 13–54.

E. Herrala et al., "Imaging Spectrometer For Process Industry Applications", SPIE, vol. 2248, pp. 32–40, (1994).

* cited by examiner

*Primary Examiner*—Steven P. Griffin
*Assistant Examiner*—Eric Hug
(74) *Attorney, Agent, or Firm*—Greenblum & Bernstein P.L.C.

(57) ABSTRACT

Process and apparatus for determining properties of a traveling material web. The process includes simultaneously illuminating a plurality of measuring points on the material web with electromagnetic radiation, and imaging, through at least one optical device, the plurality of measuring points on one detection surface of at least one detector. The device includes at least one radiation source for illuminating a plurality of measuring points on the material web, at least one detector having a detection surface, and at least one optical device for imaging of the measuring points on the detection surface of the at least one detector.

45 Claims, 4 Drawing Sheets

PROCESS AND APPARATUS FOR DETERMINING THE PROPERTIES OF A TRAVELING MATERIAL WEB

CROSS-REFERENCE TO RELATED APPLICATIONS

The present application claims priority under 35 U.S.C. § 119 of German Patent Application No. 199 12 500.7, filed on Mar. 19, 1999, the disclosure of which is expressly incorporated by reference herein in its entirety.

BACKGROUND OF THE INVENTION

1. Field of the Invention

The present invention relates to a process and apparatus for determining properties of a traveling material web, e.g., a paper web in a paper machine.

2. Discussion of Background Information

When manufacturing webs, for example, paper webs, an effort is made to obtain the greatest possible amount of information about the material web being created, in order to have the option of intervening deliberately in the manufacturing process.

It is known to take spectroscopic measurements using electromagnetic radiation in the IR range on a paper web in a paper machine to determine parameters which are relevant for the process from the interaction of the IR radiation with the paper web information. To do so, traversing measurement heads, i.e., running crosswise (transverse) to a web travel direction, are used which operate with multiple discrete wavelengths in order to inspect the paper web, e.g., with regard to moisture, basis weight, opacity, or content.

The problem with such traversing systems is the high production speed in modem manufacturing machines which, in the case of paper machines can be, e.g., on the order of 2,000 m/min. With the known traversing measurement systems, it is impossible at such high process speeds to obtain cross-direction profiles or so-called "time-shifted cross profiles," because the distribution of the respective pertinent parameters across the width of the material web cannot be determined or can be determined only with insufficient accuracy. Furthermore, the large dimensions of traversing systems are a disadvantage because they can only be used at very few locations of the machine, for example, only at the end of a paper machine.

It is also known to evaluate continuous IR spectra using different mathematical processes, in which the measurements are taken at only one location and are frequently taken with complex, expensive instruments, such as FTIR spectrometers.

Known devices and/or processes are described, e.g., in U.S. Pat. No. 4,098,641, EP-0 137 696, WO 98/36264, WO 95/08019, WO 93/15389, and WO 95/31709, the disclosures of which are expressly incorporated by reference herein in their entireties.

SUMMARY OF THE INVENTION

The present invention provides the simplest and least expensive capability for determining the properties of a traveling material web which, in particular, allows quick cross-direction profiles to be determined at selected places on the material web.

The present invention includes a plurality of measuring points on the material web that are simultaneously illuminated and imaged through at least one optical device on one detection surface divided into multiple individual detection surfaces of at least one detector.

According to the invention, multiple areas of the material web can be simultaneously inspected without contact. The division of the detection surfaces of the detector makes it possible to process or evaluate the signals generated by the imaging of the measuring points on the detection surface of the detector separately at first by measuring point and subsequently to combine them into an overall image of the material web. According to the invention, for each measurement, a partial area of the material web containing the measuring points is imaged on the detection surface of the detector. Therefore, a snapshot of the material web is obtained with each measurement. Because measurements are taken simultaneously at all measuring points according to the invention, the result can be used for a quick control and/or adjustment of the manufacturing process immediately after the measurement. In combination with sufficiently rapid processing devices, it is therefore possible to achieve continuous process monitoring with the capability of immediate correction. A quick adjustment prevents or minimizes the production of rejects and results in fewer quality fluctuations. Moreover, the quick intervention allowed by the process according to the invention can be particularly advantageous in the case of material changes or generally when changing over to another product.

According to the invention, the material webs can fundamentally be inspected with regard to every property by which the interaction of electromagnetic radiation with the material web is influenced. In manufacturing paper, e.g., the moisture content or moisture, basis weight, opacity, fiber orientation, thickness, surface properties, type and/or distribution of contents, etc., are parameters with regard to which an inspection of the paper web that is being produced or the finished product is of interest. The capability of inspecting in rapid succession each of several areas of the material web simultaneously, makes it possible, e.g., to measure the moisture of the paper web immediately after the press part of a paper machine, in order to adjust a vapor bubble box of the dry part on the basis of the measurement results.

Of course, the present invention is not limited to paper machines or to specified positions in a machine. Instead, properties of other material webs, e.g., any chosen fiber material webs, including cardboard webs as well as textile webs, which are of interest can be determined at any chosen position of the manufacturing machine.

When, according to an exemplary embodiment of the invention, the measuring points are located along a substantially straight line, it becomes possible for the material web to be line scanned using the detector and/or the optical device. In this regard, the material web can be illuminated in such a way that the straight line formed by the measuring points extends at least substantially cross-wise (or perpendicularly) to the web travel direction (i.e., the measuring points are substantially illuminated through the optical fibers). In this way, current cross-direction profiles of the material web can be obtained, in order to determine the distribution of the parameters across the width of the material web.

The use of electromagnetic radiation in the IR range to illuminate the measuring points according to another exemplary embodiment of the invention makes it possible to operate IR spectroscopy at the measuring points. This radiation is particularly appropriate for determining the moisture of paper webs. For example, radiation in the range of approximately 0.1 μm to 40 μm can be used. A preferred wavelength range is in the near-IR range and includes, e.g., wavelengths between approximately 1.0 μm and 2.5 μm.

The material web can be illuminated using appropriate sources of IR radiation in order to take reflection measurements at the illuminated measuring points, with the measurements preferably taken in diffuse reflection. It is also possible to transilluminate the material web with IR radiation and to take transmission measurements by detecting on the detector any radiation that penetrates through the material web at the respective measuring points.

According to another exemplary embodiment of the invention, each measuring point can be imaged using an optical fiber.

Using optical fibers, the radiation originating from the measuring points can be guided to any chosen place, particularly one that is spatially separated from the material web. Thus, the space required for the invention at the material web can be minimized. The process according to the invention can therefore be carried out even when space is limited and consequently, in principle, can be used at any position on a machine for manufacturing the material web. Consequently, the space available for the detector or the devices adjacent to the detector is not limited. Therefore, the invention also makes it possible to take measurements, e.g., immediately after the servo components of the machine which are used to influence manufacturing. In that way, the control systems for the process are minimized.

Instead of optical fibers, it is also possible to use a respective slit-shaped screen arrangement for illuminating the measuring points, such that the each measuring point can be imaged on the detector detection surface, and the screen arrangement can be provided with an optical device connected before or after it.

Particularly informative results can be obtained when, according to another embodiment of the invention, different wavelengths and/or wavelength ranges of the electromagnetic radiation originating from the measuring points can be detected on the detector in chronological succession, e.g., periodically.

In one example, the wavelengths 2.05 μm, 1.95 μm, and 1.83 μm are detected successively on the detector. Particularly when determining the moisture of paper webs, such measurements provide informative results and are particularly advantageous in the low-moisture range. In any application, it can be ensured according to the invention that the only radiation that is detected on the detector is that from which information can be obtained about the parameters that are of interest for the material web.

For measurements related to wavelength, a filter unit including a plurality of filter elements having different wavelength selectivity can be connected before the detector. The filter elements can be distributed in the circumferential direction on a rotating disk, to be brought into the radiation path in chronological succession by the rotation of the disk, which operates in the manner of a chopper. Such a filter unit or chopper disk allows periodic selection of the respective wavelength ranges to be detected.

At least one filter element can be constructed as a graded filter in one variation of the invention. In this way, wavelengths located in succession within a continuous range of the radiation originating from the measuring points can reach the detection surface of the detector.

According to another embodiment of the invention, at least some measuring points are each imaged on exactly one individual detection surface of the detector.

The unique allocation of one measuring point to a respective individual detection surface of the detector, which is also known as a pixel, makes optimum use of the maximum position resolution that is achievable using the respective detector.

It is also possible according to the invention to image at least some measuring points simultaneously on several individual detection surfaces of the detector.

The allocation of single measuring points to multiple individual detection surfaces which, in this way, are combined to some extent to form a "superpixel," minimizes detector noises and improves the signal-to-noise ratio of the measurements. The individual detection surfaces or pixels allocated to one measuring point can be combined or connected together into a "superpixel" either as part of signal processing or evaluation or using hardware.

According to another embodiment of the invention, one or several radiation sources can be used for illumination and moved as a whole system transverse to the web travel direction or the optical device can preferably be moved relative to the material web cross-wise or approximately perpendicular to the web travel direction, with the movement preferably being periodic and, e.g., made with a small amplitude compared with the width of the material web. To do so, the radiation sources and at least the light entrance areas of the optical device, e.g., the sections of optical fibers which are each provided with one entrance surface, can be supported on a measurement crosspiece extending crosswise to the web travel direction over the width of the material web. The crosspiece can be moveably mounted in the longitudinal direction.

With a device that is moveable cross-wise to the material web, every point on the material web can be reached. In particular, as a function of the speed of the movement and the read-out of the detector signal, continuous inspection of the material web can be achieved.

According to another embodiment of the invention, signals supplied by the detector may be transmitted to a process control system for control and/or regulation of the manufacturing process of the material web.

In the process control system, the signal, which may optionally be preprocessed in an evaluation unit connected before the process control system and prepared in a computer using appropriate algorithms, can be compared with prespecified target values for the individual parameters. Based on the results of the comparison, an intervention may be made on the process control if necessary.

The present invention also includes at least one radiation source for illuminating the multiple measuring points on the material web, at least one detector having a detection surface divided into multiple individual detection surfaces, and at least one optical device for imaging the measuring points on the detection surface of the detector.

The present invention is directed to a process for determining properties of a traveling material web. The process includes simultaneously illuminating a plurality of measuring points on the material web with electromagnetic radiation, and imaging, through at least one optical device, the plurality of measuring points on one detection surface of at least one detector.

According to a feature of the invention, the one detection surface may be divided into a plurality of individual detection surfaces. Further, the material web can include a paper web.

In accordance with another feature of the invention, the process can also include arranging the measuring points to lie along a substantially straight line extending at least essentially cross-wise to a web travel direction.

According to still another feature of the instant invention, the electromagnetic radiation can be within the IR range. Further, the electromagnetic radiation can be within the near-IR range, and the electromagnetic radiation may have a wavelength range of approximately 1.0 to 2.5 $\mu$m.

In accordance with a further feature of the present invention, the imaging of the plurality of measuring points can utilize light reflected by the material web at the plurality of measuring points.

According to a still further feature of the invention, the imaging of the plurality of measuring points may utilize transilluminated light at the plurality of measuring points, and the process can further include taking transmission measurements of the transilluminated light at the plurality of measuring points.

In accordance with another feature of the invention, the imaging of at least some of the plurality of measuring points may include transmitting optical data through an optical fiber.

According to another feature of the present invention, the imaging of at least some of the plurality of measuring points can include imaging through a slit-shaped screen arrangement having an optical device coupled one of before and after the screen arrangement.

Further, the imaging of at least some of the plurality of measuring points can include detecting at least one of different wavelengths and wavelength ranges of electromagnetic radiation originating from the measuring points on the detector. The at least one of different wavelengths and wavelength ranges of electromagnetic radiation originating from the measuring points can be successively detected. Further still, the at least one of different wavelengths and wavelength ranges of electromagnetic radiation originating from the measuring points can be periodically detected.

Still further, at least one discrete radiation spectrum detected on the detector may include the wavelengths of approximately 2.05 $\mu$m, approximately 1.94 $\mu$m, and approximately 1.83 $\mu$m.

The process can also include selecting at least one of individual wavelengths and wavelength ranges of the radiation to be detected with at least one filter unit. The at least one filter unit can be positioned between the at least one optical device and the detection surface.

In accordance with another aspect of the instant invention, the measuring points may be illuminated by at least one of approximately dot-shaped and at least one line-shaped radiation source.

According to still another aspect of the present invention, the detection surface can include a plurality of individual detection surfaces, and at least some measuring points can be imaged on exactly one individual detection surface. Still further, the detection surface can include a plurality of individual detection surfaces, and at least some measuring points can be imaged on a plurality of individual detection surfaces.

At least one of at least one illuminating radiation source and the at least one optical device can be movable relative to the material web. The at least one of at least one illuminating radiation source and the at least one optical device can be movable the cross-wise to a web travel direction. The movement of the at least one of at least one illuminating radiation source and the at least one optical device may be periodic, and can have an amplitude substantially equal to a distance between measuring points.

In accordance with a further aspect of the invention, the process can further include transmitting signals from the detector to a process control system adapted for control and/or regulation of a manufacturing process of the material web. Signal preparation can occur before transmission to the process control system.

The present invention is directed to a device for determining properties of a traveling material web. The device includes at least one radiation source for illuminating a plurality of measuring points on the material web, at least one detector having a detection surface, and at least one optical device for imaging of the measuring points on the detection surface of the at least one detector.

According to a feature of the invention, the detection surface comprises a plurality of individual detection surfaces. The material web can include a paper web.

In accordance with another feature of the invention, the at least one radiation source can include at least one of a plurality of approximately dot-shaped radiation sources and at least one approximately line-shaped radiation source.

According to still another feature of the instant invention, the at least one optical device can include a plurality of optical fibers, and each of the plurality of optical fibers may be assigned to a measuring point. An entrance surface of each of the plurality of optical fibers can be positioned directly adjacent to the material web. An entrance surface of each of the plurality of optical fibers may be positioned directly adjacent the assigned measuring point. The plurality of optical fibers may include moisture-free quartz and may have a diameter of approximately 200 $\mu$m. Emergent sides of the plurality of optical fibers may be combined into an emergent surface that is at least approximately adapted to a shape of the detection surface. The emergent surface can be slit-shaped.

In accordance with a further feature of the invention, the at least one detector can include a line detector, and the detection surface may be strip-shaped. The detection surface may be divided into a plurality of pixels.

The device can also include a filter unit coupled before the at least one detector. The filter unit can include a plurality of filter elements having different wavelength selectivity. The plurality of filter elements can be successively positioned into an optical path. The filter elements may be circumferentially distributed on a rotatable disk.

Further, the at least one radiation source and light entrance surfaces of the at least one optical device may be combined into a measurement unit arranged to extend across at least substantially an entire width of the material web and cross-wise to a web travel direction. The measurement unit may be movable cross-wise to the web travel direction.

The present invention is directed to a device for determining properties of a traveling material web. The device includes at least one radiation source for illuminating a plurality of measuring points on the material web, at least one detector having a detection surface having a plurality of pixels, and at least one optical device for imaging of the measuring points on the detection surface of the at least one detector. The at least one optical device may include a plurality of optical fibers, wherein each optical fiber can be assigned to a respective measuring point. The plurality of optical fibers can include entrance surfaces positioned adjacent the respective measuring point, and emergent sides coupled to provide images of the measuring points on the detection surface. A filter device can be positioned between the emergent sides and the detection surface.

According to an aspect of the invention, the filter device may include a rotatable disk including circumferentially spaced filters. Between the spaced filters, the rotatable disk can be opaque to radiation.

In accordance with yet another feature of the instant invention, some of the plurality of optical fibers are associated with only one pixel, and other of the plurality of optical fibers are associated with more than one pixel.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
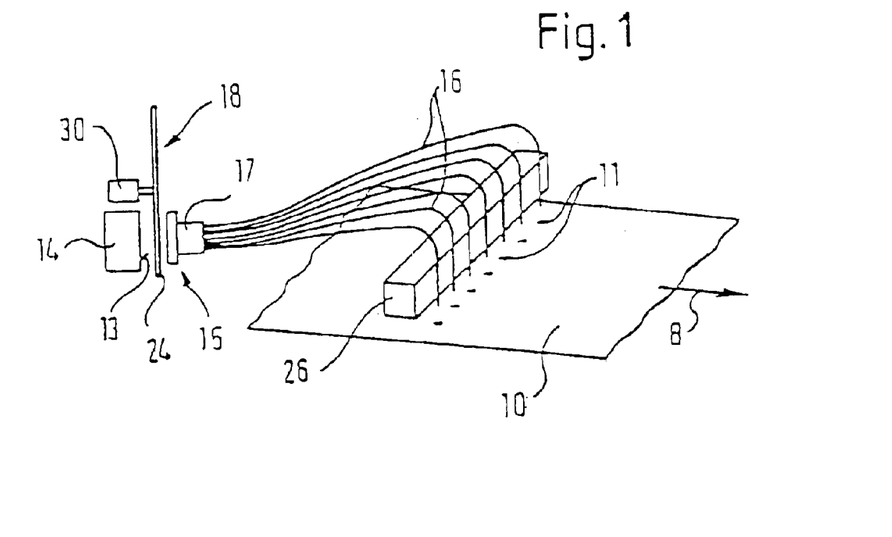
FIG. 1 illustrates a schematic view of a device positioned adjacent a paper web in accordance with the instant invention.

FIG. 1 illustrates a schematic view of the structure of a measuring device according to the invention for performing the measurement process according to the invention.

The arrangement includes a measurement unit 26 constructed as a measurement crosspiece, which is arranged to extend over or across a paper web 10 and cross-wise to a web direction B. Measurement unit 26 is provided with a plurality of, e.g., approximately dot-shaped radiation sources (not shown), each of which emits electromagnetic radiation in the IR range, preferably in the near-IR range, e.g., with wavelengths in the range of approximately 1.0 μm to 2.5 μm.

The radiation sources illuminate circular areas on paper web 10 which depicted in FIG. 1 as measuring points 11 and illustrated as dots. Measuring points 11 are located along a substantially straight line extending cross-wise to web travel direction B. Fundamentally, any number of radiation sources and, therefore, measuring points 11 can be utilized to illuminate a strip-shaped-area on paper web 10.

It is also possible, for illumination or transillumination of paper web 10, to use one or more radiation sources, each of which has a strip or slit-shaped light emergent surface, at the measuring points to be inspected. For this purpose, optical fibers can be utilized.

On measurement crosspiece 26, a plurality of optical fibers 16 can be distributed in the cross-wise direction having light entrance surfaces disposed directly adjacent to paper web 10 to illuminate measuring points 11 via the radiation sources. Optical fibers 16 are positioned such that the radiation emitted from the radiation sources that is reflected at measuring points 11 enters the associated optical fiber 16, which guides the radiation to an optical device 15 disposed on an emergent side.

Figure 1A:
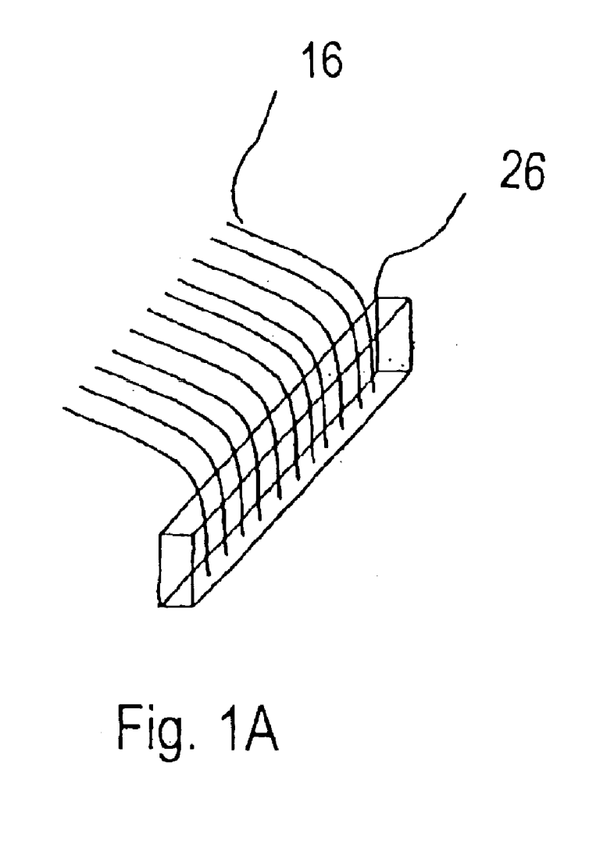
FIG. 1A illustrates a schematic view of an alternative arrangement for bundling the optical fibers for illuminating the material web.
Figure 1B:
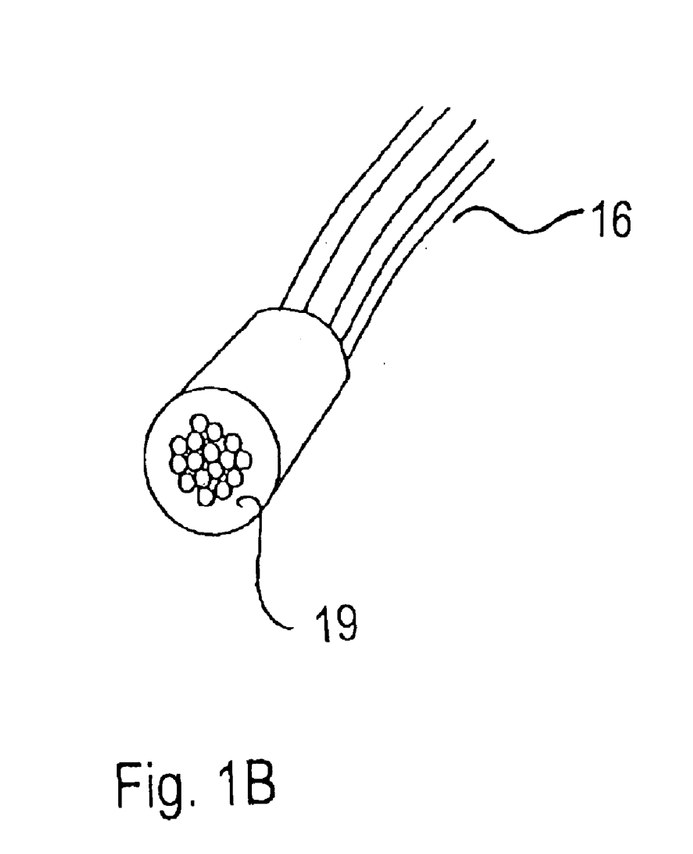
FIG. 1B illustrates a schematic view of another alternative arrangement for bundling the optical fibers for illuminating the material web.

As shown in FIG. 1, the optical fibers can be coupled to crosspiece 26. In an alternative arrangement, as illustrated in FIG. 1A, optical fibers 16 can extend into and/or through crosspiece 26. Further, crosspiece 26 can be formed from a material that is transparent to the radiation. In another alternative, as illustrated in FIG. 1B, optical fibers 16 can be bundled together in a housing 19. In a known manner, housing 19 can be mounted for movement cross-wise to the web travel direction.

The ends of optical fiber 16 on the emergent side are combined in a case 17 such that an emergent surface is formed by the individual emergent surfaces of optical fibers 16. The emergent surface can be adapted to the type of detector 14 to be used, and is described in greater detail below in reference to FIGS. 4 and 5.

A commercially-available line detector is preferably used as detector 14, whose detection surface is formed from IR-sensitive photoconductors, for example, photodiodes.

Moisture-free quartz fibers having a diameter of approximately 200 μm are preferably used as optical fibers 16, although other optical fibers can be used. The dimensions, particularly the diameter, of optical fibers 16 can be adapted to division of detection surface 13 of detector 14.

Figures 8A, 8B:
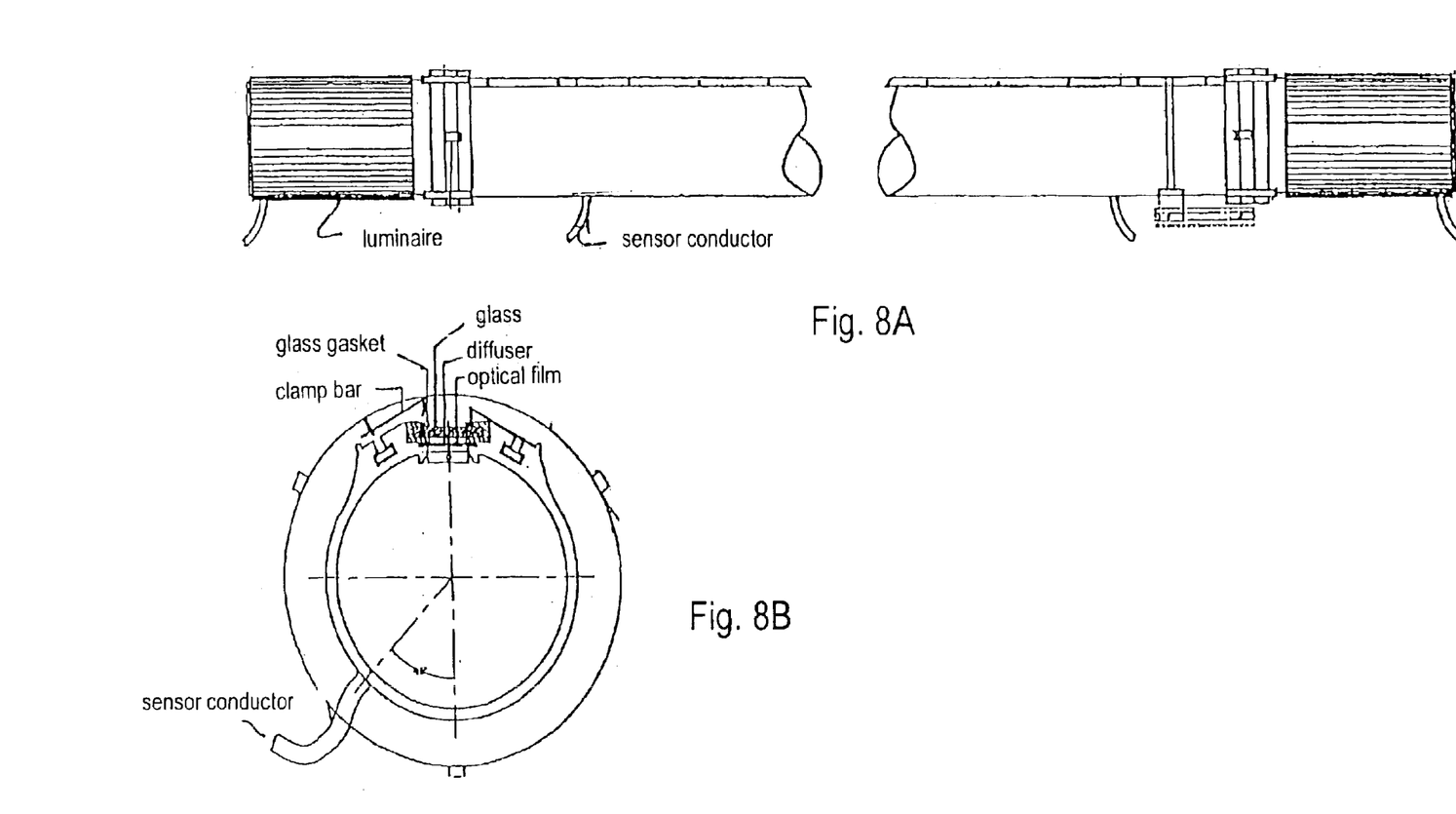
FIGS. 8A and 8B illustrate schematic views of a slit-shaped screen for illuminating the material web.

Instead of optical fibers 16, it is also possible to use, as illustrated in FIGS. 8A and 8B, a slit-shaped screen, e.g., a double ended Iridis pipe manufactured by the company TIR, to illuminate measuring points 11 so that respective measuring points 11 of paper web 10 can be imaged on an appropriately disposed detector. Further, an optical device can be positioned next to the slit-shaped screen, e.g., before or after the it.

Figure 6:
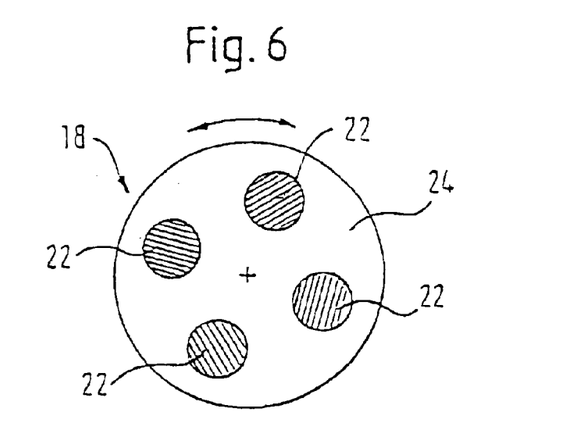
FIG. 6 illustrates a schematic top view of a filter unit.

A disk 24 of a filter unit 18 can be positioned between optical device 15 and detection surface 13 of detector 14. Disk 24 can be rotatably driven using a commercially-available dc motor. Disk 24, which is described in greater detail below in reference to FIG. 6, is provided with different wavelength-selective filter elements, which are distributed in the circumferential direction.

Figure 7:
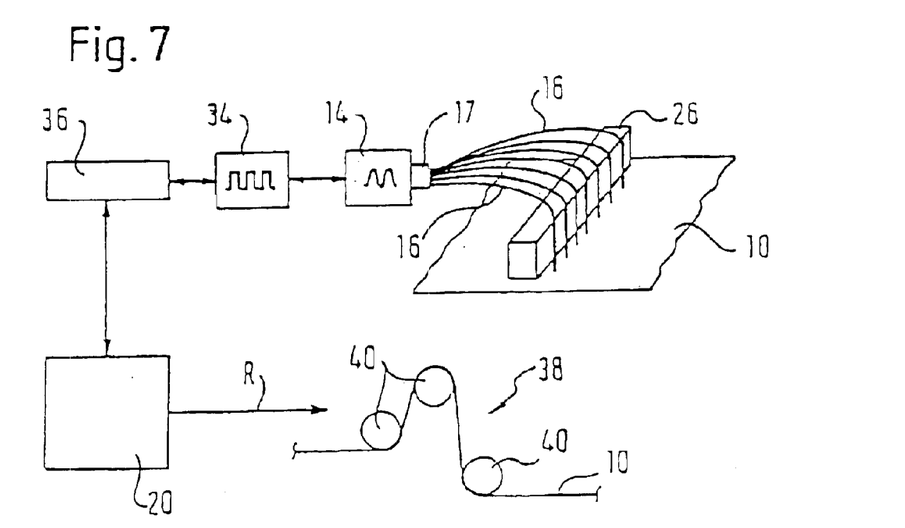
FIG. 7 illustrates a schematic view of the device coupled to a control and/or regulation system.

Devices disposed after detector 14, e.g., for processing and evaluating the detector signals, are explained in relation to FIG. 7.

Figure 2:
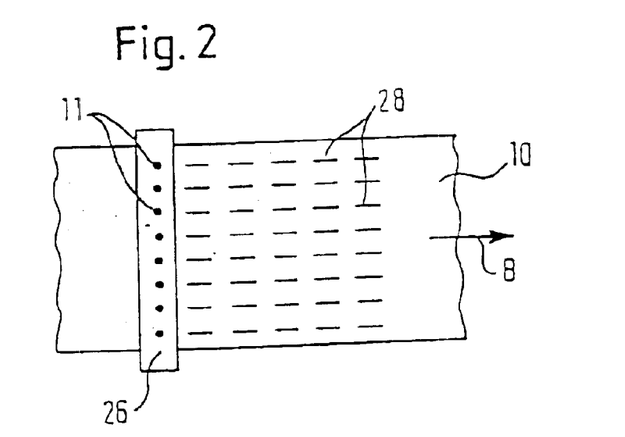
FIG. 2 illustrates a schematic top view of a portion of the device depicted in FIG. 1.

FIG. 2 illustrates measurement lines 28 on paper web 10 indicating those areas of paper web 10 traveling through or under measurement unit 26 which were previously illuminated and, therefore, inspected by the device according to the invention.

The breaks in measurement lines 28, each of which is allocated to one radiation source or one measuring point 11, which are present in web travel direction B, indicate that the measurement can be taken discontinuously, e.g., such that either the radiation sources are alternately switched on and off or that there are dead times for the read-out of detector 14 between individual measurements. Such short measurement pauses can be created by switching among different filter elements of one filter unit. Further, the discontinuity can be provided where a chopper is a vital part of the optical device. During the measurement pauses, reference measurements can also be taken, as explained below.

Figure 3:
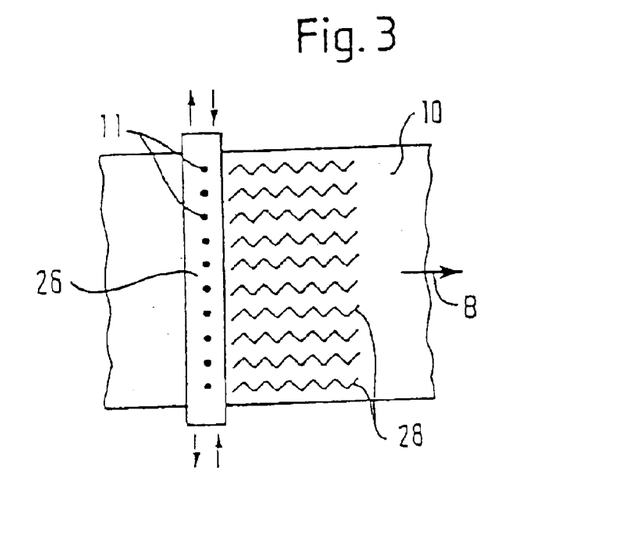
FIG. 3 illustrates a schematic top view of a portion of the device depicting cross-wise movement of the device.

An example of a continuous measurement which results in unbroken measurement lines 28 is illustrated in FIG. 3. In this embodiment, measurement unit 26 may be periodically moved relative to the paper web 10 and cross-wise to web travel direction B during the measurement, as shown by the arrows. The movement of measuring device 26 is made with a small amplitude, compared to the width of paper web 10, so that measurement lines 28 do not intersect. The periodic movements of measurement unit 26 which produce the zigzag-shaped measurement lines 28 could alternatively be made in such a way that sinusoidal measurement lines 28 are produced. Moreover, it is also possible to utilize the cross-wise movement of measurement unit 26 with discontinuous measurement by using, e.g., a chopper as part of the optical device.

The movement of measurement unit 26 relative to paper web 10 has the advantage that paper web 10 can be completely sampled in the cross-wise direction without requiring a fundamental change in the design of the measurement device.

Figures 4, 5:
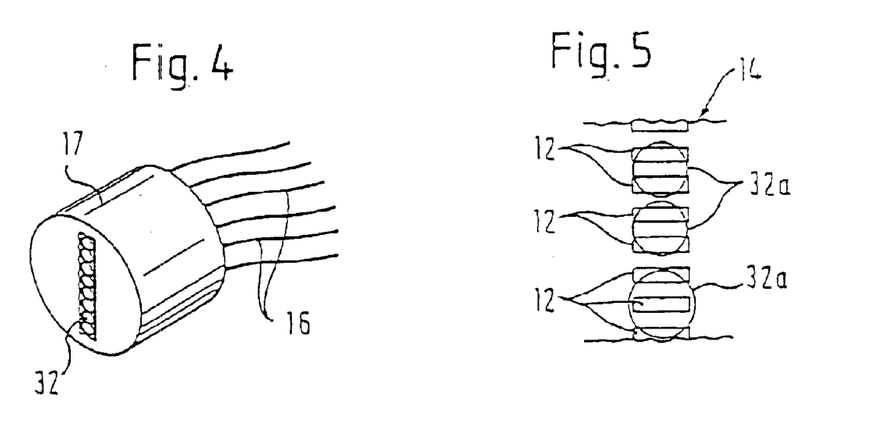
FIG. 4 illustrates a schematic view of an end section of an optical device.
FIG. 5 illustrates a schematic view of a part of a detection surface of a detector.

FIG. 4 illustrates case 17 in which the end sections of optical fibers 16 on the emergent side are combined so that individual emergent surfaces 32 of optical fibers 16 lie along a substantially straight line and together form an approximately strip-shaped emergent surface of the optical device. The length of the emergent surface is designed so as not to exceed the corresponding dimension of detection surface 13 of detector 14 (see FIG. 1), which enables imaging of all individual emergent surfaces 32 of optical fibers 16, and, therefore, all measuring points 1 1, on detector detection surface 13. In the slit of case 17, which is provided for optical fibers 16, optical fibers 16 may be arranged one above the other or adjacent each other in a sequence that corresponds to the sequence of the light entrance surfaces disposed across measuring points 11 on paper web 10.

FIG. 5 illustrates images 32a of individual emergent surfaces 32 of optical fibers 16 and, therefore, measuring points 11 on detection surface 13 of detector 14. Detection surface 13 can be divided into rectangular individual detection surfaces or pixels 12, which are each formed by an individual detector that is sensitive to IR, e.g., a photoconductor or a photodiode.

Individual emergent surfaces 32 of optical fibers 16 may be imaged on multiple pixels 12 of the partially-shown detector 14. In this case, the top two images 32a are shown on two pixels 12 and the bottom image 32a is shown on three pixels 12. Pixels 12 that are allocated to a same optical fiber 16 can be combined or connected together-using software or hardware. While an improved signal-to-noise ratio is obtained in this manner, it is also possible according to the invention to image each individual emergent surface 32 or measuring point 11 on only one individual pixel, which can provide maximum position resolution using respective detector 14. Whether the imaging occurs on one or more pixels 12 depends, e.g., on the diameter of optical fibers 16 and on the design of detection surface 13. The imaging properties of the arrangement according to the invention can also be influenced by optical device 15.

FIG. 6 illustrates a top view of filter disk 24 of filter unit 18, which includes, e.g., four circular filter elements 22 evenly distributed in the circumferential direction. Each filter element 22 is transparent to radiation having an individual wavelength or wavelengths located within a narrow window. From the radiation that strikes disk 24, which can rotate in one or both directions, respective individual or multiple discrete wavelengths that can be detected on detector 14 can be successively filtered out. When this is done, wavelength selection occurs periodically due to rotation of the disk. The number, type, and/or arrangement of filter elements 22 on disk 24 are fundamentally variable and are selected according to the individual requirements. A set of replaceable chopper disks 24 can also be provided.

Instead of individual filter elements 22, it is also possible to integrate into disk 24 at least one, e.g., semicircular graded filter, which therefore covers an angle of rotation of 180°, so that the wavelength selectivity of disk 24 continuously changes during rotation.

Disk 24, according to FIG. 6, can be provided with individual filter elements 22 and can operate in the manner of a chopper. Further, disk 24 can be rotatably driven, e.g., using a commercially-available dc motor. In connection with measurement control, disk 24 or filter unit 18 may preferably be designed as a "master" in such a way that each individual measurement is not triggered by a control unit until the appropriate rotational position of disk 24 is attained and filter element 22 or a space that is used for a reference measurement, which is opaque to the radiation, is located in the optical path. A step motor can also be used to control the rotary motion of disk 24.

The reference measurements taken between filter elements 22, i.e., at disk 24, can be used to prevent a dc drift of detector 14 and to take full advantage of the dynamic range of detector 14. In this regard, the dark current of detector 14 can be corrected on the basis of the reference signal.

According to FIG. 7, an evaluation and control unit 34 can be arranged after detector 14, in which the signals supplied by detector 14 are prepared for further processing and in which the sequence of measurements including operation of the filter unit 18 (not shown) can be controlled.

The signal can be digitized in detector 14 or in an evaluation and control unit 34. In a computer 36, the signals or data are further processed using appropriate algorithms. Those algorithms include, for example, minimum-maximum process, chemometric methods, fuzzy algorithms, and neuronal networks. Before using evaluation algorithms, the signals can undergo an equalization process, in order to equalize any differences in the response behavior of individual pixels or pixels combined into groups or individual detection surfaces 12 of detector 14. Such an equalization function can also be performed using hardware.

In a process control system 20 communicating with computer 36, the prepared data are compared with appropriate target values for the individual parameters with regard to which paper web 10 is inspected. Therefore, if necessary, control and/or adjustment parameters can be calculated which can be used as a basis for an intervention in the manufacturing process as shown by arrow R in FIG. 7, e.g., by activating appropriate servo components.

On the basis of the paper web properties determined at measuring points 11, it is possible according to the invention to optimize operation of paper machine 38, which is illustrated in FIG. 7 by a paper web 10 guided by a plurality of rolls 40, or a portion thereof.

One advantage of the present invention is that commercially-available components can be used, e.g., for the radiation sources, optical fibers 16, filter unit 18, driving motor 30, and detector 14. According to the instant invention, this provides a capability of supplying particularly inexpensive but informative results for determining the properties of material webs and for rapid process control.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

LIST OF REFERENCE CHARACTERS

10 Material web, paper web
11 Measuring point
12 Individual detection surface, pixel
13 Detection surface
14 Detector
15 Optical device
16 Optical fiber
17 Case
18 Filter unit
19 Housing
20 Process control system
22 Filter element
24 Disk
26 Measurement unit
28 Measurement line
30 Motor
32 Individual emergent surface
32*a* Image of individual emergent surface
34 Evaluation and control unit
36 Computer
38 Paper machine
40 Roller
B Web travel direction
R Control and/or regulation

What is claimed:

1. A process for determining properties of a traveling material web comprising:
   simultaneously illuminating a plurality of measuring points on the material web with electromagnetic radiation; and
   imaging, through at least one optical device, the plurality of measuring points on one detection surface of at least one detector,
   wherein the electromagnetic radiation is within the IR range.

2. The process in accordance with claim 1, wherein the one detection surface is divided into a plurality of individual detection surfaces.

3. The process in accordance with claim 1, wherein the material web comprises a paper web.

4. The process in accordance with claim 1, further comprising arranging the measuring points to lie along a substantially straight line extending at least essentially crosswise to a web travel direction.

5. The process in accordance with claim 1, wherein the imaging of the plurality of measuring points utilizes light reflected by the material web at the plurality of measuring points.

6. The process in accordance with claim 1, wherein the imaging of the plurality of measuring points utilizes transilluminated light at the plurality of measuring points, and the process further comprises taking transmission measurements of the transilluminated light at the plurality of measuring points.

7. The process in accordance with claim 1, wherein the imaging of at least some of the plurality of measuring points includes transmitting optical data through an optical fiber.

8. The process in accordance with claim 1, wherein the imaging of at least some of the plurality of measuring points includes imaging through a slit-shaped screen arrangement having an optical device coupled one of before and after the screen arrangement.

9. The process in accordance with claim 1, wherein the imaging of at least some of the plurality of measuring points includes detecting at least one of different wavelengths and wavelength ranges of electromagnetic radiation originating from the measuring points on the detector.

10. The process in accordance with claim 9, wherein the at least one of different wavelengths and wavelength ranges of electromagnetic radiation originating from the measuring points are successively detected.

11. The process in accordance with claim 10, wherein the at least one of different wavelengths and wavelength ranges of electromagnetic radiation originating from the measuring points are periodically detected.

12. The process in accordance with claim 1, wherein at least one discrete radiation spectrum detected on the detector includes the wavelengths approximately 2.05 $\mu$m, approximately 1.94 $\mu$m, and approximately 1.83 $\mu$m.

13. The process in accordance with claim 1, further comprising selecting at least one of individual wavelengths and wavelength ranges of the radiation to be detected with at least one filter unit.

14. The process in accordance with claim 13, wherein the at least one filter unit is positioned between the at least one optical device and the detection surface.

15. The process in accordance with claim 1, wherein the measuring points are illuminated by at least one of approximately dot-shaped and at least one line-shaped radiation source.

16. The process in accordance with claim 1, wherein the detection surface comprises a plurality of individual detection surfaces, and
   wherein at least some measuring points are each imaged on exactly one individual detection surface.

17. The process in accordance with claim 1, wherein the detection surface comprises a plurality of individual detection surfaces, and
   wherein at least some measuring points are imaged on a plurality of individual detection surfaces.

18. The process in accordance with claim 1, wherein at least one of at least one illuminating radiation source and the at least one optical device is movable relative to the material web.

19. The process in accordance with claim 18, wherein the at least one of at least one illuminating radiation source and the at least one optical device is movable the cross-wise to a web travel direction.

20. The process in accordance with claim 19, wherein the movement of the at least one of at least one illuminating radiation source and the at least one optical device is periodic, and has an amplitude substantially equal to a distance between measuring points.

21. The process in accordance with claim 1, further comprising transmitting signals from the detector to a process control system adapted for control and/or regulation of a manufacturing process of the material web.

22. The process in accordance with claim 21, wherein signal preparation occurs before transmission to the process control system.

23. The process in accordance with claim 1, wherein the illumination and imaging occur simultaneously.

24. A apparatus for determining properties of a traveling material web comprising:
- at least one radiation source for illuminating, in the IR range, a plurality of measuring points on the material web;
- at least one detector having a detection surface; and
- at least one optical device for imaging of the measuring points on the detection surface of the at least one detector.

25. The apparatus in accordance with claim 24, wherein said detection surface comprises a plurality of individual detection surfaces.

26. The apparatus in accordance with claim 25, wherein the material web comprises a paper web.

27. The apparatus in accordance with claim 24, wherein said at least one radiation source comprises at least one of a plurality of approximately dot-shaped radiation sources and at least one approximately line-shaped radiation source.

28. The apparatus in accordance with claim 24, wherein said at least one optical device comprises a plurality of optical fibers, wherein each of the plurality of optical fibers is assigned to a measuring point.

29. The apparatus in accordance with claim 28, wherein an entrance surface of each of the plurality of optical fibers is positioned directly adjacent to the material web.

30. The apparatus in accordance with claim 28, wherein an entrance surface of each of the plurality of optical fibers is positioned directly adjacent the assigned measuring point.

31. The apparatus in accordance with claim 28, wherein said plurality of optical fibers comprise moisture-free quartz and have a diameter of approximately 200 $\mu$m.

32. The apparatus in accordance with claim 28, wherein emergent sides of said plurality of optical fibers are combined into an emergent surface that is at least approximately adapted to a shape of said detection surface.

33. The apparatus in accordance with claim 32, wherein said emergent surface is slit-shaped.

34. The apparatus in accordance with claim 24, wherein said at least one detector comprises a line detector, and said detection surface is strip-shaped.

35. The apparatus in accordance with claim 34, wherein said detection surface is divided into a plurality of pixels.

36. The apparatus in accordance with claim 24, further comprising a filter unit coupled before said at least one detector, said filter unit comprising a plurality of filter elements having different wavelength selectivity.

37. The apparatus in accordance with claim 36, wherein said plurality of filter elements are successively positionable into an optical path.

38. The apparatus in accordance with claim 36, wherein said filter elements are circumferentially distributed on a rotatable disk.

39. The apparatus in accordance with claim 24, wherein said at least one radiation source and light entrance surfaces of said at least one optical device are combined into a measurement unit arranged to extend across at least substantially an entire width of the material web and cross-wise to a web travel direction.

40. The apparatus in accordance with claim 39, wherein said measurement unit is movable cross-wise to the web travel direction.

41. A apparatus for determining properties of a traveling material web comprising:
- at least one radiation source for illuminating a plurality of measuring points on the material web;
- at least one detector having a detection surface having a plurality of pixels;
- at least one optical device for imaging of the measuring points on the detection surface of the at least one detector;
- said at least one optical device comprising a plurality of optical fibers, wherein each optical fiber is assigned to a respective measuring point;
- said plurality of optical fibers comprising entrance surfaces positioned adjacent said respective measuring point, and emergent sides coupled to provide images of the measuring points on said detection surface; and
- a filter device positioned between said emergent sides and said detection surface.

42. The apparatus in accordance with claim 41, wherein said filter device comprises a rotatable disk including circumferentially spaced filters.

43. The apparatus in accordance with claim 42, wherein between said spaced filters, said rotatable disk is opaque to radiation.

44. The apparatus in accordance with claim 41, wherein some of said plurality of optical fibers are associated with only one pixel, and
wherein other of said plurality of optical fibers are associated with more than one pixel.

45. The apparatus in accordance with claim 41, wherein the at least one radiation source supplies radiation in the IR range.

* * * * *